(12) United States Patent
Neumann

(10) Patent No.: US 11,599,921 B2
(45) Date of Patent: Mar. 7, 2023

(54) SYSTEM AND METHOD FOR DETERMINING AN ALIMENTARY PREPARATION PROVIDER

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/106,699

(22) Filed: Nov. 30, 2020

(65) Prior Publication Data

US 2022/0172262 A1 Jun. 2, 2022

(51) Int. Cl.
*G06Q 30/06* (2012.01)
*G06Q 30/02* (2012.01)
*G06Q 10/06* (2012.01)
*G06N 20/00* (2019.01)
*G16H 20/60* (2018.01)
(Continued)

(52) U.S. Cl.
CPC ......... *G06Q 30/0605* (2013.01); *G06N 20/00* (2019.01); *G06Q 10/06315* (2013.01); *G06Q 30/0205* (2013.01); *G06Q 30/0639* (2013.01); *G16H 40/20* (2018.01); *G16H 50/20* (2018.01); *G16H 20/60* (2018.01)

(58) Field of Classification Search
CPC ............. G06N 20/00; G06Q 10/06315; G06Q 30/0205; G06Q 30/06–0645; G06Q 30/08; G06Q 50/01; G16H 20/60; G16H 40/20; G16H 50/20
See application file for complete search history.

(56) References Cited

U.S. PATENT DOCUMENTS 6,859,215 B1 2/2005 Brown
9,129,289 B2 * 9/2015 Vaughn .................. G06Q 30/06
(Continued)

OTHER PUBLICATIONS

Machine Learning and AI in Food Industry: Solutions and Potential; by: Olena Kovalenko; Date Jan. 29, 2020.
(Continued)

*Primary Examiner* — Adam L Levine
(74) *Attorney, Agent, or Firm* — Caldwell Intellectual Property Law

(57) ABSTRACT

A system of determining an alimentary preparation provider is disclosed. The system comprises a computing device. The computing device is configured to receive input from a user device at a current geographical location. The input comprises an alimentary request and a plurality of request parameters. The computing device generates a plurality of alimentary preparation providers as a function of the plurality of request parameters. A request parameter classifier is generated by the computing device. The computing device classifies, by the request parameter classifier, the plurality of request parameters and the plurality of alimentary preparation providers. The classification outputs an ordered list of request parameters. The computing device assigns the alimentary request to a first alimentary preparation provider as a function of an ordered list of request parameters. A method for determining an alimentary preparation provider is disclosed.

20 Claims, 6 Drawing Sheets

(51) Int. Cl.
    *G06Q 30/0601*     (2023.01)
    *G16H 50/20*     (2018.01)
    *G16H 40/20*     (2018.01)
    *G06Q 30/0204*     (2023.01)
    *G06Q 10/0631*     (2023.01)

(56)     References Cited

U.S. PATENT DOCUMENTS

| | | | |
|---|---|---|---|
| 10,360,616 B2* | 7/2019 | Lopez | G06Q 10/00 |
| 10,366,434 B1* | 7/2019 | Belousova | G06Q 30/0627 |
| 10,586,294 B1 | 3/2020 | Wilson | |
| 10,769,523 B2* | 9/2020 | Eyster | G06N 3/0454 |
| 10,783,482 B2* | 9/2020 | Phillips | G06Q 30/0639 |
| 10,846,353 B2* | 11/2020 | Rayanchu | G06F 40/205 |
| 2003/0125249 A1 | 7/2003 | Blecha et al. | |
| 2005/0004843 A1 | 1/2005 | Heflin | |
| 2009/0307096 A1 | 12/2009 | Antonellis | |
| 2014/0257877 A1 | 9/2014 | L'Heureux | |
| 2016/0012513 A1* | 1/2016 | Martinez | G06Q 50/12 705/15 |
| 2016/0350837 A1 | 12/2016 | Williams | |
| 2016/0379293 A1 | 12/2016 | Barajas Gonzalez | |
| 2017/0278202 A1* | 9/2017 | Mimassi | G06Q 30/0635 |
| 2019/0343156 A1 | 11/2019 | Drori | |
| 2020/0098466 A1* | 3/2020 | Murdoch | H04W 4/021 |
| 2020/0342550 A1* | 10/2020 | Halimsaputera | G16H 20/60 |
| 2021/0158263 A1* | 5/2021 | Mimassi | G06Q 10/02 |

OTHER PUBLICATIONS https://www.ncr.com/restaurants/kitchen-production; Date: Sep. 2, 2020.

* cited by examiner

SYSTEM AND METHOD FOR DETERMINING AN ALIMENTARY PREPARATION PROVIDER

FIELD OF THE INVENTION

The present invention generally relates to the field of optimal resource allocation by artificial intelligence. In particular, the present invention is directed to determining an alimentary preparation provider.

BACKGROUND

Efficient routing of requests for fulfilling a food order effectively remains an elusive goal. Particularly where such actions include customization of an order and multiple issues of timing, speed, quality, and necessity affect the choice in question. Current selection and communication processes often fall short of ideal solutions.

SUMMARY OF THE DISCLOSURE

In an aspect of the disclosure, a system of determining an alimentary preparation provider is disclosed. The system comprises a computing device. The computing device is configured to receive an input from a user device at a current geographical location. The input comprises an alimentary request and a plurality of request parameters. The computing device generates a plurality of alimentary preparation providers as a function of the plurality of request parameters. A request parameter classifier is generated by the computing device. The classifier is generated by receiving parameter training data correlating the plurality of request parameters to an ordered list of request parameters and training a classification algorithm using the parameter training data. The computing device classifies, by using the request parameter classifier, the plurality of request parameters and the plurality of alimentary preparation providers. The classification outputs an ordered list of parameters. The computing device assigns the alimentary request to a first alimentary preparation provider as a function of an ordered list of request parameters.

In another aspect of the disclosure, a method of determining an alimentary preparation provider is disclosed. The method receives, by a computing device, an input from a user device at a current geographical location. The input comprises an alimentary request and a plurality of request parameters. The method generates, by the computing device, a plurality of alimentary preparation providers as a function of the plurality of request parameters. A request parameter classifier is generated by the computing device. The classifier is generated by receiving parameter training data correlating the plurality of request parameters to an ordered list of request parameters and training a classification algorithm using the parameter training data. The computing device classifies, by using the request parameter classifier, the plurality of request parameters and the plurality of alimentary preparation providers. The classification outputs an ordered list of request parameters as a function of an ordered list of request parameters. The method, by the computing device, assigns the alimentary request to a first alimentary preparation provider as a function of an ordered list of request parameters.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining an alimentary provider. A user may enter input which may include an alimentary request and a plurality of request parameters. Based on the input, a plurality of alimentary providers is created. The system may use machine-learning processes, such as the use of a classifier, to generate an ordered list of alimentary providers as a function of the request parameters, where the ordered list generates the plurality of alimentary providers in descending order based on the request parameters. The alimentary preparation provider receiving the highest order, is assigned the alimentary request.

The system and methods disclosed improve the area of placing a requesting food by allowing the user to enter a request and parameters that will serve as inputs for a machine-learning process to determine a suitable provider. In addition, it provides for load balancing where the system will transfer the alimentary request to a second provider if the first provider does not have the capacity to fulfill the alimentary request. A practical application of the disclosure allows, for example, the user to enter a composition and other parameters, and the system may suggest an alimentary provider based on the composition and other parameters.

Figure 1:
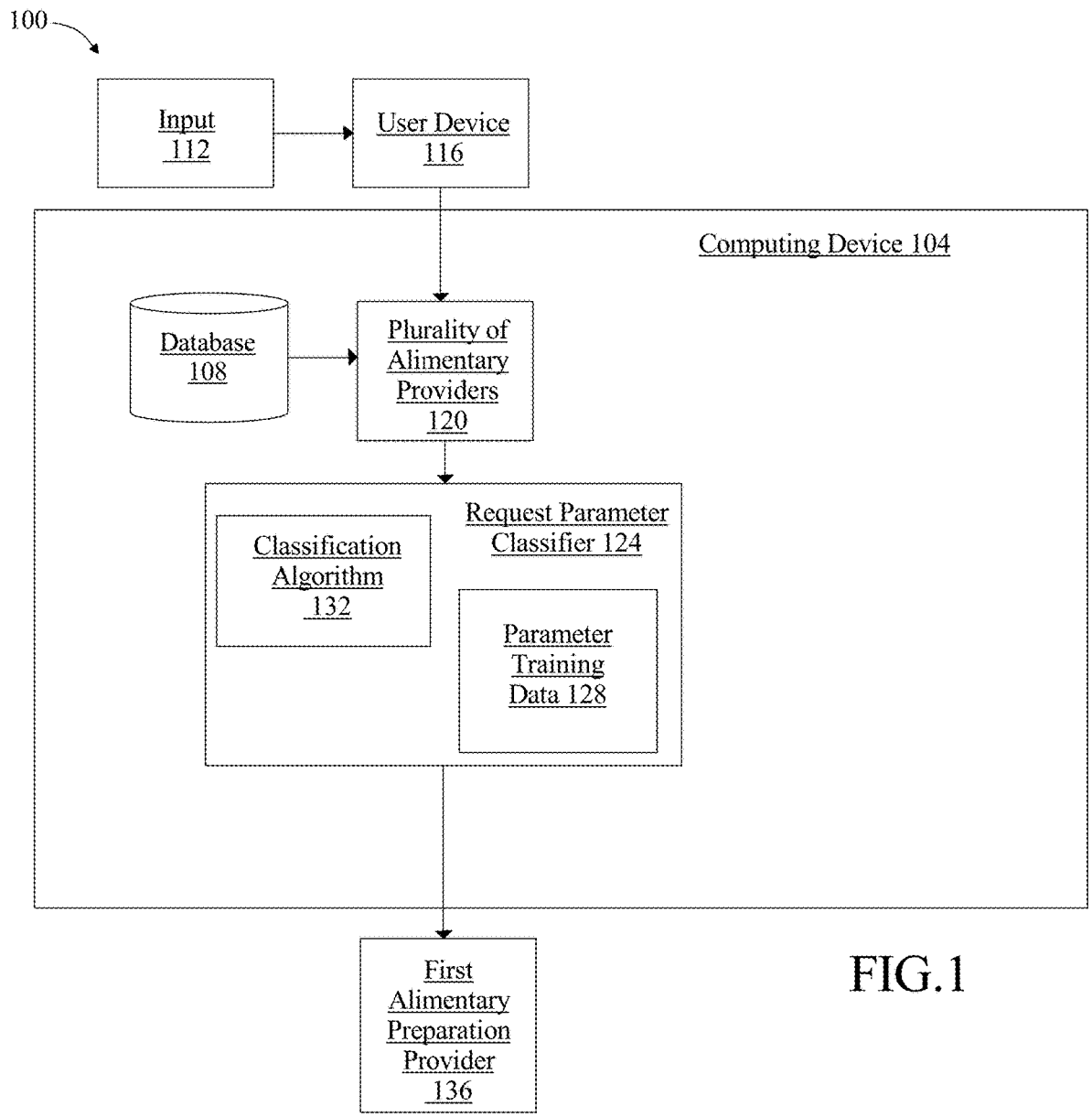
FIG. 1 is a block diagram of an exemplary embodiment of a system of determining an alimentary preparation provider.

Referring now to FIG. 1, an exemplary embodiment of a system 100 for determining an alimentary preparation provider is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may connect to and/or include a database 108. Database 108 may be implemented, without limitation, as a relational database 108, a key-value retrieval database 108 such as a NOSQL database 108, or any other format or structure for use as a database 108 that a person skilled in the art would recognize as suitable upon review of the entirety of this disclosure. Database 108 may alternatively or additionally be implemented using a distributed data storage protocol and/or data structure, such as a distributed hash table or the like. Database 108 may include a plurality of data entries and/or records as described above. Data entries in a database 108 may be flagged with or linked to one or more additional elements of information, which may be reflected in data entry cells and/or in linked tables such as tables related by one or more indices in a relational database 108. Persons skilled in the art, upon reviewing the entirety of this disclosure, will be aware of various ways in which data entries in a database 108 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 108.

Figure 2:
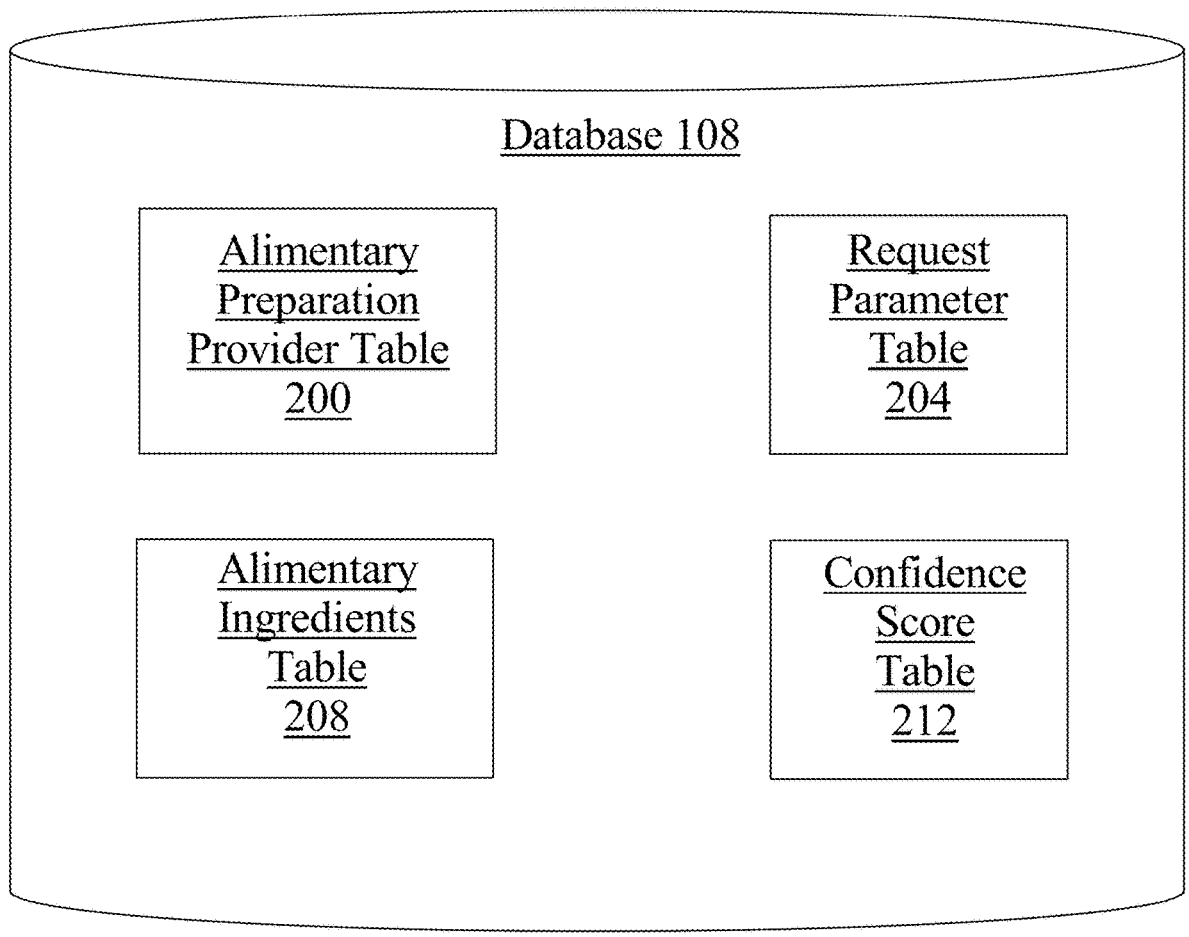
FIG. 2 is a block diagram of an exemplary embodiment of a database.

Referring now to FIG. 2 an exemplary embodiment of a database 108 is illustrated. Database 108 may, as a non-limiting example, organize data stored in the database according to one or more database tables. One or more database tables may be linked to one another by, for instance, common column values. For instance, a common column between two tables of database 108 may include an identifier of alimentary preparation providers, for instance as defined below; as a result, a query may be able to retrieve all rows from any table pertaining to a given alimentary provider. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 108 may include, as a non-limiting example, an alimentary preparation provider table 200, which may be used to store records and attributes related to alimentary preparation providers. This may include, but not limited to, names of providers, types of foods prepared, hours of operation, or the like. As another non-limiting example, one or more tables in database 108 may include a request parameters table 204 which may be used to store request parameters, such as delivery parameters, dietary parameters, and the like As another non-limiting example, one or more tables in database 108 may include an alimentary ingredients table 208. An alimentary ingredients table 208 may include, but not limited ingredients table, correlations between ingredients and types of foods, list of substitutions for ingredients, and the like. As another non-limiting example, one or more tables in database 108 may include a confidence score table 212. A confidence score table 212 may include correlations of alimentary preparation providers to confidence scores, historical confidence scores, trends on confidence scores, and the like.

Referring back to FIG. 1, computing device 104 is configured to receive input 112 from a user device 116 at a current geographical location. As used in this disclosure, a "current geographical location" is defined as a specific location, region, or place where user device 116 is located. The current geographical location may be, for example, a street, a city, a point of interest, a latitude and longitude coordinates, and the like. The location of user device 116 may be tracked by by a Global Positioning System (GPS) and used to establish the current geographical location. For example, user device 116 may be within a geographical distance from an alimentary preparation provider that may expedite a delivery of an alimentary request. Input 112 may include an alimentary request. A "user device," as used in this disclosure, is any device that a user may use to enter an input. This may include, but it is not limited to, a cell phone, a tablet computer, a laptop computer, a desktop computer, and the like. User device 116 may have the capability to connect to the Internet. The user device may be configured to use a wireless network using Wi-Fi and any available communication standard such as, for example, IEEE 802.11. User device 116 may be configured to connect to a short-range network using, for example, Bluetooth® technology. User device 116 may be configured to access a network by connecting using a wired network connection using, for example, an Ethernet connection. Additionally, user device 116 may receive an input which may include an alimentary request. An "alimentary request," is defined for the purposes of this disclosure as a combination of ingredients that an alimentary preparation provider may combine to form a meal. An alimentary request, for example, may be referred to as by name. For instance, a user may ask for a "pepperoni pizza" as an alimentary request. In another non-limiting example, a user may ask for "Matzot Balls" or "Karpas" prepared at a Kosher establishment. A user may also select an alimentary request by selecting the alimentary combination from a menu of an alimentary preparation provider. A user may also specify ingredients and a type of food, which may turn into meals. As used in this disclosure, "alimentary preparation providers" may include any entities that may fulfill the alimentary request. As a non-limiting example, an alimentary preparation provider may be a dietary specialty kitchen. For example, a dietary specialty kitchen may be equipped with proper alimentary ingredients and equipment to prepare dishes according to a dietary law such as Kosher or Halal. Other types of dietary specialty kitchens may include, but not limited to, a specialty kitchen capable of fulfilling an alimentary request based on the health condition of the user. For example, a user may be afflicted by a health condition such as Celiac's Disease where consumption of gluten may cause an adverse reaction to the user. In this case, the alimentary request for that user may be routed to a dietary specialized kitchen where no gluten is present. Another example of a dietary specialty kitchen may include a kitchen that may fulfill an alimentary request requiring the use of organic alimentary ingredients.

Additionally or alternatively, and with continued reference to FIG. 1, the alimentary preparation provider may be an independent alimentary preparation provider for other alimentary providers such as, for example, a restaurant. As a non-limiting example, a user may place an alimentary request with a particular alimentary provider. The user may specify a health condition such as an autoimmune condition requiring a specialized dietary preparation. The alimentary provider may use a dietary specialized kitchen to fulfill the alimentary request. The dietary specialty kitchen may arrange for the delivery of the alimentary request to the geographic location of user device 116. Alternatively, as the dietary specialty kitchen may be an independent contractor preparing an alimentary request for another party. The dietary specialty kitchen may deliver the alimentary request to the requesting restaurant, for example. The delivery may take place by use of a transfer party. A "transfer party," as defined in this disclosure, is a person and/or device that transports alimentary combinations to one or more users requesting alimentary combinations. Transfer party may be on foot, or traveling by vehicle, such as a car, scooter, bicycle, etc. One or more transfer parties may be directed to one or more alimentary providers to receive an order placed by users and deliver the orders to the users located at corresponding destinations, which may include without limitation residential or commercial addresses.

Additionally, and still with reference to FIG. 1, input 112 may include a plurality of request parameters. As used in this disclosure, a "request parameter" is defined as at least one parameter that may define specific conditions related to the alimentary request. For example, a request parameter may include delivery options such as, but not limited to, an expedited delivery, a delivery on a date different from the date the alimentary request is placed, a specific transfer agent, and the like. Another example of a request parameter may be a dietary restriction due to a religious observance or a health condition which may include, but not limited to, the use of a Kosher kitchen, the use of a gluten free kitchen, the use of low fat ingredients, and the like. Another example may include substitution parameters. "Substitution parameters" as defined in this disclosure are parameters that may be set to define a substitution of, for example, an ingredient, when an ingredient is not available. For example, there may be a "do not substitute" option, or there may be a "substitute with only vegan ingredients" option or "substitute with organic ingredients only" option. Request parameters may include parameters for the user to specify a specific dietary specialized kitchen. For example, for a specific dietary reason, a user may prefer the alimentary request to go to a kitchen of their choice. Input 112 may include one or a plurality of request parameters. For example, a user may select a delivery parameter and a substitution parameter. Request parameters may be selected, for example, by selecting a tick box or selecting an appropriate choice when the user is presented with multiple choices for a request parameter. Request parameters may be entered as free-from text.

With continued reference to FIG. 1, computing device 104 may generate a plurality of alimentary preparation providers 120 as a function of the plurality of request parameters. For example, based on the request parameters entered as input 112, computing device 104 may produce a corresponding plurality of alimentary preparation providers 120 which may correspond to the plurality of request parameters. Plurality of alimentary preparation providers 120 may match a single or a plurality of request parameters. Plurality of alimentary preparation providers 120 may be within a threshold distance relative to the current geographical location of user device 116. As used in this disclosure, a "threshold distance" is a value, in miles or other units of length, that is either manually entered by the user or automatically selected by computing device 104 based on user history which serves as the maximum distance between plurality of alimentary preparation providers 120 and user device 116. In a non-limiting example, computing device 104 may default to a threshold distance of "0.5 miles." Using threshold distance of 0.5 miles will output a plurality of alimentary preparation providers 120 which are within 0.5 miles of user device 116. The user may customize and expand the threshold distance to, for example, "10 miles" where computing device will output alimentary preparation provider candidates which are within 10 miles of user device 116. A user may enter a range of values for the threshold distance. For example, a user may enter "0.5-1.0 miles which will output alimentary preparation provider candidates that are within 0.5 and 1.0 miles of user device 116.

Referring still to FIG. 1, computing device 104 may generate a request parameter classifier 124. Computing device 104 receives parameter training data 128 correlating the plurality of request parameters to an ordered list of request parameters received by alimentary preparation providers. The vector training set may be received as a function of user-entered valuations of request parameter elements, parameter metrics, and/or measurable values. The vector training set may be received by one or more past iterations of the previous request parameter vectors. The vector training set may be received by one or more remote devices that at least correlate an request parameter metric to a measurable value, wherein a remote device is an external device to computing device 104. Each request parameter of the ordered list of request parameters is ordered in descending order as a function of a historical selection. The ordered list may request parameters ordered by the frequency of their selection. For example, a request parameter such as "only use organic ingredients" may be ordered higher if it has been selected by users at a higher frequency. A historical selection may include, but not limited to the frequency of selection of a request parameter. A historical selection may include parameters ordered by the priority by users. For example, a user may choose a delivery parameter and weigh them higher than a dietary request parameter. Classification algorithm 132 is trained using parameter training data 128. "Training data," as used herein, is data containing correlations that a machine-learning process may use to model relationships between two or more categories of data elements. For instance, and without limitation, training data 128 may include a plurality of data entries, each entry representing a set of data elements that were recorded, received, and/or generated together; data elements may be correlated by shared existence in a given data entry, by proximity in a given data entry, or the like. Multiple data entries in training data 128 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 128 according to various correlations; correlations may indicate causative and/or predictive links between categories of data elements, which may be modeled as relationships such as mathematical relationships by machine learning processes as described in further detail below. Training data 128 may be formatted and/or organized by categories of data elements, for instance by associating data elements with one or more descriptors corresponding to categories of data elements. As a non-limiting example, training data 128 may include data entered in standardized forms by persons or processes, such that entry of a given data element in a given field in a form may be mapped to one or more descriptors of categories. Elements in training data 128 may be linked to descriptors of categories by tags, tokens, or other data elements; for instance, and without limitation, training data 128 may be provided in fixed-length formats, formats linking positions of data to categories such as comma-separated value (CSV) formats and/or self-describing formats such as extensible markup language (XML), enabling processes or devices to detect categories of data.

Alternatively or additionally, and with continued reference to FIG. 1, training data 128 may include one or more elements that are not categorized; that is, training data 128 may not be formatted or contain descriptors for some elements of data. Machine learning algorithms and/or other processes may sort training data 128 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 128 to be made applicable for two or more distinct machine learning algorithms as described in further detail below. Training data 128 used by computing device 104 may correlate any input data as described in this disclosure to any output data as described in this disclosure. Training data may contain entries, each of which correlates a machine learning process input to a machine learning process output, for instance without limitation, one or more elements of biological extraction data to a taste index. Training data may be obtained from previous iterations of machine-learning processes, user inputs, and/or expert inputs.

With continued reference to FIG. 1, computing device 104 may classify, using request parameter classifier 124, the plurality of request parameters and the plurality of alimentary preparation providers 120. The classification outputs an ordered list of request parameters in descending order. For example, by using request parameter classifier 124 which has been trained with parameter training data 128, and with inputs that may include plurality of alimentary preparation providers 120 and the plurality of request parameters, a determination as to an alimentary preparation provider that may fulfill the alimentary request may be made. A detailed description as to classification using a machine-learning process is described below in this disclosure. For example, computing device may rank the plurality of alimentary preparation providers 120 based on an objective function. An "objective function," as used in this disclosure, is a mathematical function used by a computing device 104 to score a quantitative element or factor which may include, for example, any request parameter. In various embodiments a score of a particular factor may be based on a combination of one or more factors. Each factor may be assigned a score based on predetermined variables, for example, a delivery request parameter may be scored higher than a dietary request parameter.

Additionally or alternatively, and will continued reference to FIG. 1, in some embodiments, the assigned scores may be weighted or unweighted. Computing device 104 may compute a score associated with each factor and select factors to minimize and/or maximize the score, depending on whether an optimal result is represented, respectively, by a minimal and/or maximal score. Objective function may be formulated as a linear objective function, which computing device 104 may solve using a linear program such as without limitation a mixed-integer program. A "linear program," as used in this disclosure, is a program that optimizes a linear objective function, given at least a constraint. For instance, an alimentary combination factor may be constrained to values resulting from an alimentary combination suitable for consumption with a user with a certain health condition. In various embodiments, system 100 may determine scores that maximizes a total score subject to at least a constraint. An objective function may then be optimized to generate an alimentary preparation provider able to fulfill the alimentary request. Computing device 104 may assign the alimentary request to first alimentary preparation provider 136 by classification using request parameter classifier 124. For example, a user may make an alimentary request with includes a parameter of "Kosher." A certain alimentary preparation provider may receive the highest order based on receiving the highest score. As a non-limiting example, the alimentary preparation provider may have received the highest score based on having the higher frequency of selection as a Kosher restaurant.

Figure 3:
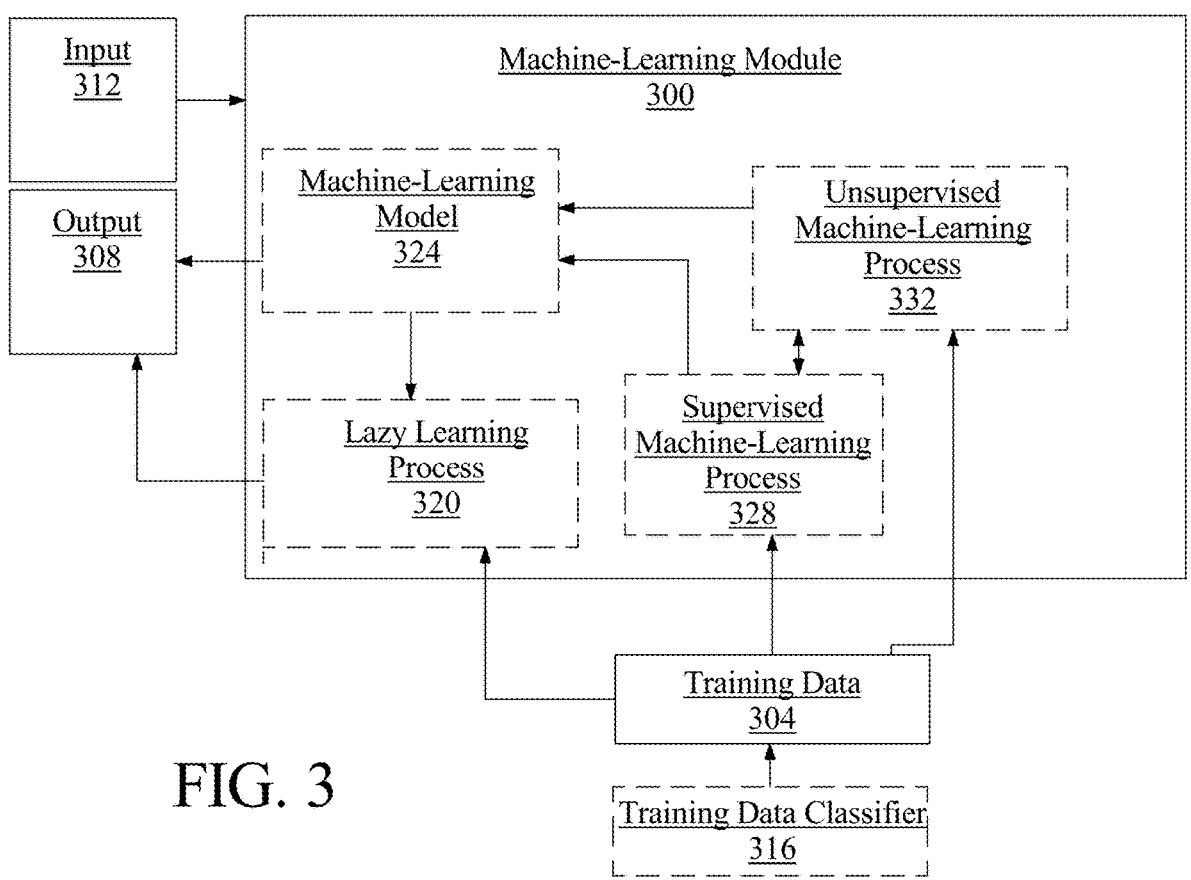
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as described earlier, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, a plurality of alimentary ingredients may serve as inputs which outputs an alimentary request.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to classify a plurality of alimentary preparation providers by a dietary restriction. Use of a classifier may, for example, classify alimentary preparation providers as Kosher or non-Kosher.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a plurality of ingredients and a type of food as described above as inputs, an alimentary request as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Now with reference back to FIG. 1, computing device 104 may be configured to output the first assigned alimentary preparation provider to user device 116. Computing device 104 may receive input from user device 116 where the input includes an acceptance of the first assigned alimentary preparation provider. Computing device 104 may receive input from user device 116 where the input includes a rejection of the first assigned alimentary preparation provider. For example, a user may be under the believe that the first assigned alimentary preparation provider does not satisfy the inputted request parameters. In an embodiment, the alimentary request may be assigned to a second alimentary preparation provider upon rejection of the first assigned alimentary provider. As a non-limiting example, upon rejection of the first assigned alimentary provider, the second alimentary preparation provider may be selected as a function of the ordered list of alimentary preparation providers. In another embodiment, the second alimentary preparation provider may be selected by computing device 104 by repeating any of the steps described earlier in this disclosure for assigning an alimentary request to the first preparation provider. In another embodiment, the approximate time of delivery of the alimentary request to the geographical location of user device may be outputted to the user device 116. For example, user device 116 may receive a live status update about the location of the transfer agent selected to transfer the alimentary combination to the location of user device 116. The update may include a color depiction as to the status of the delivery as a function of a total time which may include the preparation time of the alimentary request by the alimentary preparation provider and the transfer by the alimentary preparation provider to the user or to another party which may then transfer the alimentary request to the user. As an example, the graphical user interface may show the transfer path in green if the transfer agent is on time to deliver the alimentary combination at the prescribed time based on the alimentary combination total time. In another non-limiting example, the graphical user interface may show the transfer path in yellow, if the time based on the alimentary combination total time is trending to a later delivery than the original delivery based on the alimentary combination total time. A yellow color may, in a non-limiting example, indicate a delivery time that is 5-15 later than the original delivery based on the alimentary combination total time. A red color may, for example, indicate a delivery time that is greater than 15 minutes than the original delivery based on the alimentary combination total time.

Still with reference to FIG. 1, computing device 104 may assign the alimentary request to first alimentary preparation provider 136 by outputting a plurality of ingredients to prepare the alimentary request. As a non-limiting example, an alimentary request may include a plurality of ingredients and a parameter that the ingredients used be all organically grown. Based on the parameter, first alimentary preparation provider 136 may be assigned. As another non-limiting example, the plurality of ingredients may include a list of ingredients to prepare a certain ethnic dish. The request parameter may indicate that "no substitutions allowed." First alimentary preparation provider 136 may be selected on the availability of the ingredients. Computing device 104 may output a confidence score by first alimentary provider 136 as a function of the plurality of ingredients. A "confidence score," as used in this disclosure, is a numerical score that describes the alimentary preparation provider's likelihood that the order will be fulfilled as requested by the user. The confidence score may be reported in a scale of, for example 1 to 10. The confidence score may be reported as a star review, where, for example, a five-star review may indicate a strong likelihood that the alimentary request may be fulfilled as expected by the user, whereas a two-star review may indicate a weak likelihood that the alimentary request may be fulfilled as requested by the user. In an embodiment, the plurality of request parameters may include a confidence score. Computing device 104 may output the confidence score to user device 116. In a further embodiment, a confidence score classifier may be trained with a classification algorithm and confidence score data correlating historical scores with alimentary preparation providers. The confidence score classifier will then classify confidence scores by using confidence scores received by a particular alimentary preparation provider and alimentary preparation and output a true confidence score for an alimentary preparation provider. The use of machine-learning models and classification algorithms has been described earlier in this disclosure.

Figure 4:
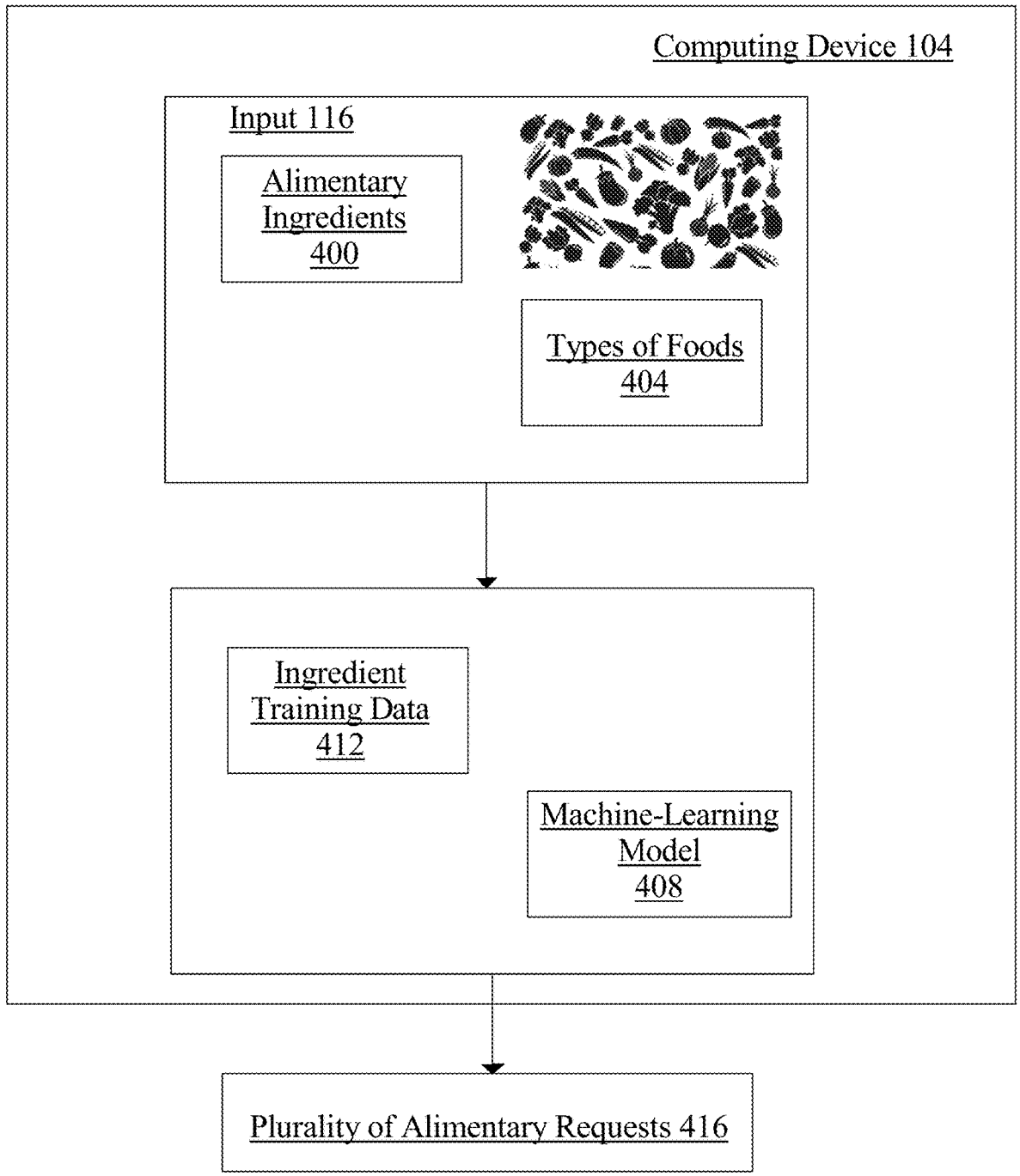
FIG. 4 is a block diagram of an exemplary embodiment of a determination of a plurality of alimentary requests as a function of a plurality of ingredients and types of foods.

Now with reference to FIG. 4, computing device 104 may be configured to receive a plurality of alimentary ingredients 400 and types of foods 404 as input 112. A user may be familiar with certain types of alimentary ingredients and a type of food but may not be familiar with the name of a dish that uses the ingredients in that particular type of food. As an example, a user may input "shrimp, tomatoes, and paprika" as alimentary ingredients and "creole" as the type of food. Additionally, computing device 104 may receive ingredient training data. The vector training set may be received as a function of user-entered valuations of ingredient elements, ingredient metrics, and/or measurable values. The vector training set may be received by one or more past iterations of the previous ingredient vectors. The vector training set may be received by one or more remote devices that at least correlate an ingredient element and types of foods metric to a measurable value, wherein a remote device is an external device to computing device 104. For example, computing device 104 may train a machine-learning model 408 using ingredient training data 412 correlating the plurality of ingredients and the types of foods to the alimentary request. Computing device 104 may output a plurality of alimentary request 416 as a function of machine-learning model 408. Computing device may display plurality of alimentary request 416 in user device 116. Computing device 104 may receive input 112 from a user with an alimentary request as a function of the plurality of alimentary requests.

Referring back to FIG. 1, computing device 104 may be configured to regenerate the parameter training data 128 as a function of the plurality of alimentary parameters. For example, request parameters may be entered as free-form text. A machine learning model that may employ natural language processing may be used to extract request parameters from free-from text. One of ordinary skill in the art would understand how to implement an algorithm to extract the request parameters using a machine-learning model implementing natural language processing. For example, named entity recognition tools may be used to extract the entities in the text. Named entity recognition (NER) may identify entities such as locations and food requests. In addition, topic modeling may be used to extract request parameters from free-form text. For example, a Latent Dirichlet Allocation method may be implemented. This technique may identify the request parameters based on a request topic, such as, but not limited to a delivery topic, a dietary topic, and the like. Computing device 104 may retrain the request parameter training data using the regenerated parameter training data.

With continued reference to FIG. 1, computing device 104 may be configured to receive input from the first assigned alimentary preparation provider. The input may include a number of alimentary requests assigned to the first alimentary preparation provider. For example, based on plurality of request parameters and the alimentary request, computing device 104 may assign the alimentary request to a particular alimentary preparation provider. The particular alimentary preparation provider may have reached capacity as to how many alimentary requests they can fulfill. Computing device 104 may assign the alimentary request to a second alimentary preparation provider as a function of the number of alimentary requests assigned to the first alimentary preparation provider. Computing device 104 may assign the alimentary request to a second alimentary provider based on a threshold of orders that may be prepared by the alimentary preparation provider. For example, computing device 104 may receive a threshold value for the number of orders an alimentary preparation provider may fulfill in a specified time frame such as a particular hour of the day, in a day, during a rush period, and the like. Computing device 104 may query the alimentary preparation provider for the actual number of orders that the alimentary preparation provider is currently handling or in the fulfillment queue. Computing device 104 may compare the threshold value for the number of orders the alimentary preparation provider may fulfill against the actual number of orders that the alimentary provider is currently handling and re-route an a future alimentary request if the actual number of orders under fulfillment exceeds the threshold value. Computing device 104 may transmit a message to user device 116 to indicate that the alimentary request has been re-routed to a second alimentary preparation provider.

Alternatively, or additionally, and with continued reference to FIG. 1, the input may include a type of alimentary requests assigned to the first alimentary preparation provider. Computing device 104 may assign the alimentary request to a second alimentary preparation provider as a function of the type of alimentary request assigned to the first alimentary provider. For example, based on plurality of request parameters which may include a type of food, and the alimentary request, computing device 104 may assign the alimentary request to a particular alimentary preparation provider. The particular alimentary preparation provider may not be prepared to fulfill the alimentary request based on the type of food. Computing device 104 may assign the alimentary request to a second alimentary preparation provider as a function of the type of food assigned to the first alimentary preparation provider. For example, computing device 104 may assign to first alimentary preparation provider 136 an alimentary request which requires the type of food to be "spicy food." First alimentary preparation provider 136 may not be prepared to fulfill an alimentary request that includes a "spicy" type of food. Computing device 104 may assign the alimentary request to a second alimentary preparation provider that may be ready to fulfill an order requiring the food type to be spicy.

With continued reference to FIG. 1, computing device 104 may be configured to receive a geographical parameter of the first alimentary preparation provider. As used in this disclosure, a "geographical parameter" is a parameter that identifies a location of an alimentary provider. For example, a geographical parameter may include, but not limited to, a physical street address, GPS coordinates, physical landmarks that may be used to triangulate the first alimentary preparation provider, and the like. A geographical parameter may include a threshold distance value between the first and the second alimentary preparation provider. Computing device 104 may receive geographical parameter training data. The vector training set may be received as a function of user-entered valuations of geographic elements, geographic metrics, and/or measurable values. The vector training set may be received by one or more past iterations of the previous geographic vectors. The vector training set may be received by one or more remote devices that at least correlate a geographic element and types of foods metric to a measurable value, wherein a remote device is an external device to computing device 104. The geographical parameter training data correlates geographical parameters with alimentary preparation providers. The implementation of training data has been described earlier in this disclosure. Computing device 104 may train a geographical parameter classifier using geographical parameter training data. Computing device 104 may classify, using a classification algorithm, a second alimentary preparation provider as a function of geographical parameter and the first alimentary preparation provider. The use of a classifier has been described earlier in this disclosure.

Figure 5:
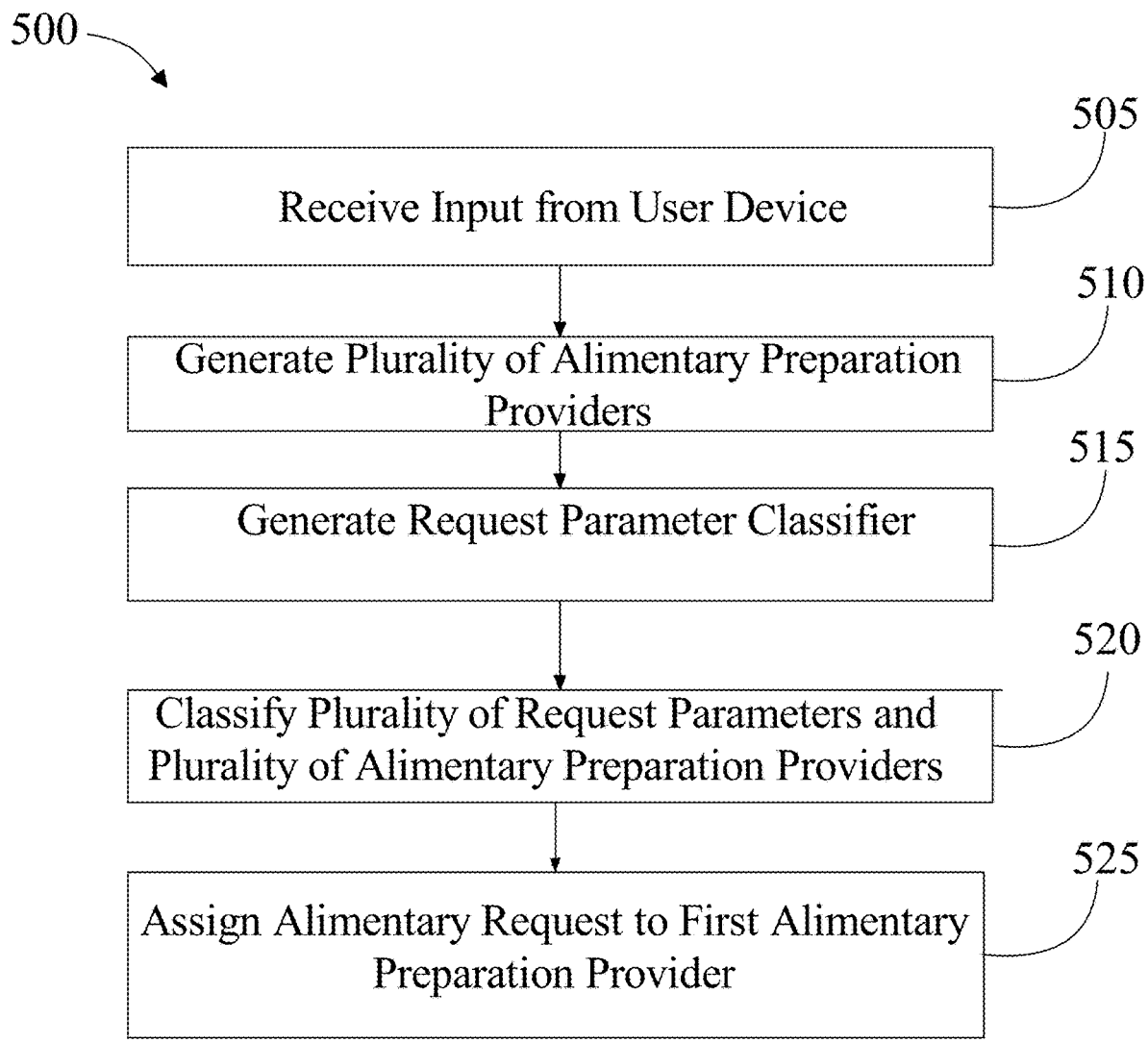
FIG. 5 is a flow diagram illustrating an exemplary embodiment of a method of determining an alimentary preparation provider.

Now with reference to FIG. 5, an exemplary embodiment of method 500 of determining an alimentary preparation provider is illustrated. At step 505, computing device may receive an input from a user device at a current geographical location. The input may include an alimentary request and a plurality of request parameters. The alimentary request may include a plurality of ingredients that may be combined by an alimentary preparation provider to form a meal. This step may be implemented, without limitation, as described in FIGS. 1-4. The alimentary preparation provider may be an independent alimentary preparation provider for other alimentary providers such as, but not limited to, a restaurant. Additionally, the input may include a plurality of request parameters.

With continued reference to FIG. 5, computing device may include a plurality of request parameters which may include delivery options, dietary restrictions, substitution parameters, and the like. This step may be implemented, without limitation, as described in FIGS. 1-4.

Still with reference to FIG. 5, at step 510, computing device may generate a plurality of alimentary preparation providers as a function of the plurality of request parameters. This step may be implemented, without limitations, as described in FIGS. 1-4. For example, based on the request parameters entered as input, computing device may produce a corresponding plurality of alimentary preparation providers which may correspond to the plurality of request parameters.

With continued reference to FIG. 5, at step 515, computing device may generate a request parameter classifier. Computing device receives parameter training data correlating the plurality of request parameters to an ordered list of request parameters received by alimentary preparation providers. Each request parameter of the ordered list of request parameters is ordered in descending order as a function of a historical selection. Classification algorithm is trained using parameter training data 128. This step may be implemented, without limitation, as described in FIGS. 1-4.

Still with reference to FIG. 5, at step 520, computing device may classify, using the request parameter classifier, the plurality of request parameters and the plurality of alimentary preparation providers. The classification outputs the plurality of alimentary preparation providers in descending order as a function of an ordered list of request parameters. For example, by using request parameter classifier 124 which has been trained with parameter training data 128, and with inputs that may include the plurality of alimentary preparation providers and the plurality of request parameters, a determination as to an alimentary preparation provider that may fulfill the alimentary request may be made. This step may be implemented, without limitation, as described in FIGS. 1-4.

Still with reference to FIG. 5, at step 525, computing device may assign the alimentary request to first alimentary preparation provider 136 by classification using request parameter classifier 124. This step may be implemented, without limitation, as described in FIGS. 1-4.

Additionally or alternatively, and with continued reference to FIG. 5, computing device may assign the alimentary request to a first alimentary preparation provider by outputting a plurality of ingredients to prepare the alimentary request. As a non-limiting example, an alimentary request may include a plurality of ingredients and a parameter that the ingredients used be all organically grown. Based on the parameter, first alimentary preparation provider may be assigned. Computing device may output a confidence score by the first alimentary preparation provider as a function of the plurality of ingredients. This may be implemented, without limitations, as described in FIGS. 1-4.

With continued reference to FIG. 5, computing device may be configured to receive a plurality of alimentary ingredients and a type of food as input. Computing device may train a machine-learning process using ingredient training data correlating the plurality of ingredients and the types of foods to the alimentary request. Computing device may output a plurality of alimentary requests as a function of the machine-learning model. Computing device may display the plurality of alimentary requests in the user device. Computing device may receive the input from the user with an alimentary request as a function of the plurality of alimentary requests. This may be implemented, without limitations, as described in FIGS. 1-4.

With continued reference to FIG. 5, computing device may be configured to regenerate the parameter training data as a function of the plurality of alimentary parameters. Computing device may retrain the request parameter training data using the regenerated parameter training data. This may be implemented, without limitations, as described in FIGS. 1-4.

Still with reference to FIG. 5, computing device may be configured to receive input from the first assigned alimentary preparation provider. The input may include a number of alimentary requests assigned to the first alimentary preparation provider. Computing device 104 may assign the alimentary request to a second alimentary preparation provider as a function of the number of alimentary requests assigned to the first alimentary preparation provider. Computing device may assign the alimentary request to a second alimentary provider based on a threshold of orders that may be prepared by the alimentary preparation provider. Computing device 104 may query the alimentary preparation provider for the actual number of orders that the alimentary preparation provider is currently handling or in the fulfillment queue. Computing device may compare the threshold value for the number of orders the alimentary preparation provider may fulfill against the actual number of orders that the alimentary provider is currently handling and re-route an a future alimentary request if the actual number of orders under fulfillment exceeds the threshold value. Computing device may transmit a message to user device 116 to indicate that the alimentary request has been re-routed to a second alimentary preparation provider. The above may be implemented, without limitations, as described in FIGS. 1-4.

Still with reference to FIG. 5, the input may include a type of alimentary requests assigned to the first alimentary preparation provider. Computing device 104 may assign the alimentary request to a second alimentary preparation provider as a function of the type of alimentary request assigned to the first alimentary provider. Computing device 104 may assign the alimentary request to a second alimentary preparation provider as a function of the type of food assigned to the first alimentary preparation provider. The above may be implemented, without limitations, as described in FIGS. 1-4.

With continued reference to FIG. 5, computing device may be configured to receive a geographical parameter of the first alimentary preparation provider. Computing device may receive geographical parameter training data. The geographical parameter training data correlates geographical parameters with alimentary preparation providers. The implementation of training data has been described earlier in this disclosure. Computing device 104 may train a geographical parameter classifier using geographical parameter training data. Computing device 104 may classify, using a classification algorithm, a second alimentary preparation provider as a function of geographical parameter and the first alimentary preparation provider. The use of a classifier has been described earlier in this disclosure. The above may be implemented, without limitation, as described in FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
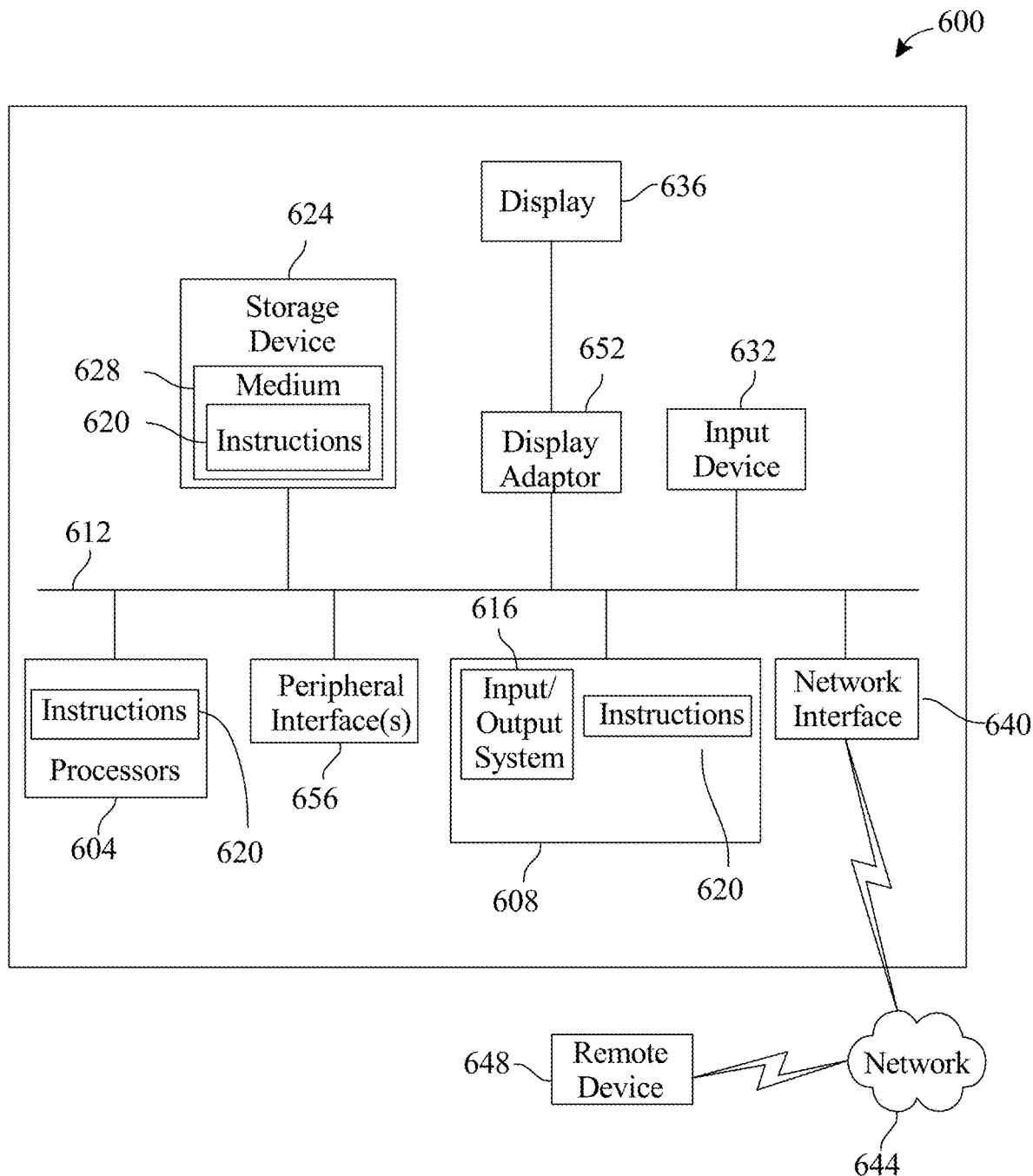
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system of determining an alimentary preparation provider, the system comprising:
a computing device configured to:
receive an input from a user device at a current geographical location, wherein the input comprises:
an alimentary request;
a plurality of request parameters; and
a geographical parameter, wherein the geographical parameter includes a threshold distance;
generate a geographical parameter classifier, wherein generating the geographical parameter classifier comprises:
generating the geographical parameter classifier using a classification algorithm;
receiving geographical parameter training data correlating geographical parameters to a plurality of alimentary providers, the geographical parameter training data comprising previous outputs of the geographical parameter classifier;
training, iteratively, the geographical parameter classifier using the geographical parameter training data;
generate a plurality of alimentary preparation providers as a function of the plurality of request parameters and the trained geographical parameter classifier;
generate a request parameter classifier, wherein generating the request parameter classifier comprises:
creating a request parameter training data set comprising the plurality of request parameters and the plurality of alimentary preparation providers correlated to an ordered list of request parameters; and
training the request parameter classifier using the parameter training data;
classify, using the trained request parameter classifier, the plurality of request parameters and the plurality of alimentary preparation providers to the ordered list of request parameters, wherein the classifying using the request parameter classifier comprises ranking the plurality of alimentary preparation providers based on an objective function;
output the ordered list of request parameters as a function of classifying the trained request parameter classifier; and
assign the alimentary request to a first alimentary preparation provider as a function of the ordered list of request parameters, wherein assigning the alimentary request further comprises outputting a plurality of ingredients to prepare the alimentary request.

2. The system of claim 1, wherein the computing device is further configured to:
receive the plurality of alimentary ingredients and a type of food as the input;
train a machine-learning model using ingredient training data correlating alimentary ingredients and types of food to alimentary requests;
output a plurality of alimentary requests as a function of the alimentary ingredients and type of food and the machine-learning model;
display the plurality of alimentary requests in the user device; and
receive an alimentary request as a function of the plurality of alimentary requests.

3. The system of claim 1, wherein the computing device is further configured to:
regenerate the parameter training data as a function of the plurality of alimentary parameters; and retrain the request parameter training data using the regenerated parameter training data.

4. The system of claim 1, wherein the plurality of alimentary preparation providers is within a threshold distance relative to a current geographical location of the user device.

5. The system of claim 1, wherein the computing device is further configured to:
receive input from the first alimentary preparation provider, wherein the input comprises a number of alimentary requests assigned to the first alimentary preparation provider; and
assign the alimentary request to a second alimentary preparation provider as a function of the number of alimentary requests assigned to the first alimentary preparation provider.

6. The system of claim 1, wherein the computing device is further configured to:
receive input from the first alimentary preparation provider, wherein the input comprises a type of alimentary request assigned to the first alimentary preparation provider; and
assign the alimentary request to a second alimentary preparation provider as a function of the type of alimentary requests assigned to the first alimentary preparation provider.

7. The system of claim 1, wherein the computing device is further configured to:
receive a geographical parameter of the first alimentary preparation provider;
receive geographical parameter training data correlating geographical parameters to alimentary preparation providers;
train a geographical parameter classifier as a function of geographical parameter training data, and
identify a second alimentary preparation provider using the geographical parameter classifier as a function of geographical parameter and the first alimentary preparation provider.

8. The system of claim 1, wherein the computing device is further configured to output the first alimentary preparation provider to the user device.

9. The system of claim 1, wherein assigning the alimentary request to the first alimentary preparation provider further comprises:
outputting a plurality of ingredients to prepare alimentary request; and
outputting a confidence score by the first alimentary preparation provider as a function of the plurality of ingredients.

10. The system of claim 9, wherein the confidence score is outputted to the user device.

11. A method of determining an alimentary preparation provider, the method comprising:
receiving, by a computing device, an input from a user device at a current geographical location, wherein the input comprises:
an alimentary request;
a plurality of request parameters; and
a geographical parameter, wherein the geographical parameter includes a threshold distance;
generating, by the computing device, a geographical parameter classifier, wherein
generating the geographical parameter classifier comprises:
generating the geographical parameter classifier using a classification algorithm;
receiving geographical parameter training data correlating geographical parameters to a plurality of alimentary providers, the geographical parameter training data comprising previous outputs of the geographical parameter classifier; and
training, iteratively, the geographical parameter classifier using the geographical parameter training data;
generating, by the computing device, a plurality of alimentary preparation providers as a function of the plurality of request parameters and the trained geographical parameter classifier;
generating, by the computing device, a request parameter classifier, wherein generating the request parameter classifier comprises:
creating a request parameter training data set comprising the plurality of request parameters and the plurality of alimentary preparation providers correlated to an ordered list of request parameters; and
training the request parameter classifier as a function of the parameter training data and a classification algorithm;
classifying, by the computing device, using the request parameter classifier, the plurality of request parameters and the plurality of alimentary preparation providers, to the ordered list of request parameters, wherein the classifying using the request parameter classifier comprises ranking the plurality of alimentary preparation providers based on an objective function;
outputting, by the computing device, the ordered list of request parameters as a function of classifying using the trained request parameter classifier; and
assigning, by the computing device, the alimentary request to a first alimentary preparation provider as a function of the ordered list of request parameters, wherein assigning the alimentary request further comprises outputting a plurality of ingredients to prepare the alimentary request.

12. The method of claim 11, further comprising:
receiving the plurality of alimentary ingredients and a type of food as the input;
training a machine-learning model using ingredient training data correlating alimentary ingredients and types of food to alimentary requests; and
outputting a plurality of alimentary requests as a function of the alimentary ingredients and type of food and the machine-learning model;
displaying the plurality of alimentary requests in the user device; and
receiving an alimentary request as a function of the plurality of alimentary requests.

13. The method of claim 11, further comprising:
regenerating the parameter training data as a function of the plurality of alimentary parameters; and
retraining the request parameter using the regenerated parameter training data.

14. The method of claim 11, wherein the plurality of alimentary preparation providers is within a threshold distance relative to the current geographical location of the user device.

15. The method of claim 11, further comprising:
receiving input from the first alimentary preparation provider, wherein the input comprises a number of alimentary requests assigned to the first alimentary preparation provider; and assigning the alimentary request to a second alimentary preparation provider as a function of the number of alimentary requests assigned to the first alimentary preparation provider.

16. The method of claim 11, wherein the computing device is further configured to:
receiving input from the first alimentary preparation provider, wherein the input comprises a type of alimentary requests assigned to the first alimentary preparation provider; and
assigning the alimentary request to a second alimentary preparation provider as a function of the type of alimentary requests assigned to the first alimentary preparation provider.

17. The method of claim 11, further comprising:
receiving a geographical parameter of the first alimentary preparation provider;
receiving geographical parameter training data;
training a geographical parameter classifier as a function of geographical parameter training data, and identifying a second alimentary preparation provider as a function of geographical parameter training data and the first alimentary preparation provider.

18. The method of claim 11, wherein the computing device is further configured to output the first alimentary preparation provider to the user device.

19. The method of claim 11, wherein assigning the alimentary request to the first alimentary preparation provider further comprises:
outputting a plurality of ingredients to prepare alimentary request;
outputting a confidence score by the first alimentary preparation provider as a function of the plurality of ingredients; and
receiving by the user device the confidence score.

20. The method of claim 11, further comprising displaying the first alimentary preparation provider in the user device.

* * * * *